United States Patent [19]

Manghisi et al.

[11] Patent Number: 4,533,748

[45] Date of Patent: Aug. 6, 1985

[54] PROCESS FOR THE OPTICAL RESOLUTION OF THE DL-α-HYDROXY-3-(4-METHOXYPHENYL)-3-(2-AMINOPHENYLTHIO)PROPIONIC ACID

[75] Inventors: Elso Manghisi; Giuseppe Cascio, both of Monza, Italy

[73] Assignee: Istituto Luso Farmaco D'Italia s.p.a., Milan, Italy

[21] Appl. No.: 539,840

[22] Filed: Oct. 7, 1983

[30] Foreign Application Priority Data

Oct. 15, 1982 [IT] Italy ................................ 23769 A/82

[51] Int. Cl.$^3$ .................. C07D 281/02; C07C 149/20
[52] U.S. Cl. ............................. 562/401; 260/239.3 B
[58] Field of Search ................. 562/401; 260/239.3 B

[56] References Cited

PUBLICATIONS

Chemical Abstracts I vol. 74: 141721(a), Abstracting Kugita et al., "Chem. Pharm. Bull." (1971), vol. 19, No. 3, pp. 595–602.
Chemical Abstracts II vol. 90: 6431(w), Abstracting Japan Tokyo Koho 78 18,038 Jun. 13, 1978.

*Primary Examiner*—Robert T. Bond
*Attorney, Agent, or Firm*—Bucknam and Archer

[57] ABSTRACT

The dl-α-2-hydroxy-3-(4-methoxyphenyl)-3-(2-aminophenylthio)propionic acid, which is a useful intermediate for the synthesis of pharmacologically active compounds, is separated in its enantiomers through salification with L-lysine with high yields and optical purities.

4 Claims, No Drawings

PROCESS FOR THE OPTICAL RESOLUTION OF THE DL-α-HYDROXY-3-(4-METHOXYPHENYL)-3-(2-AMINOPHENYLTHIO)PROPIONIC ACID

The invention refers to a method for the optical resolution of the dl-α-2-hydroxy-3-(4-methoxyphenyl)-3-(2-aminophenylthio)propionic acid having formula I (wherein the hydrogen atoms of the two asymmetric carbons are in the erythro form), useful intermediate for the preparation of optically active benzothiazepines and namely of cis(+)-2-(4-methoxyphenyl)-3-acetoxy-5-[2-(dimethylamino)ethyl]-2,3-dihydro-1,5-benzothiazepin-4(5H)-one, having formula (II), whose coronaro-dilating properties are known

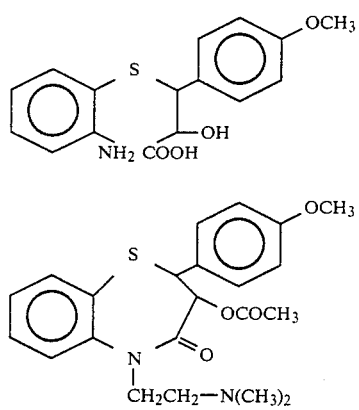

It is known that said dl-α-aminoacid can be separated in its enantiomers by salification with 1-ephedrin.

The results of this method, nevertheless, are not satisfactory, as for both the yields and the purity of the obtained product.

It has now been surprisingly found, and it is an object of the present invention, that by using L-lysine as resolution agent and operating in aqueous methanol it is possible to recover, with advantageous yields and in the pure state, the less soluble L-lysine salt of the d-α-aminoacid (enantiomer useful in the synthesis of II). By concentrating the mother liquors, the L-lysine salt of the optically impure 1-α-aminoacid is recovered. Thereafter, from the optically active L-lysine salts, the corresponding optically active aminoacids can be easily obtained by treatment with diluted organic or inorganic acids.

Therefore starting from the d-α-2-hydroxy-3-(4-methoxyphenyl)-3-(2-aminophenylthio)propionic acid obtained according to the process of the present invention, it is possible to obtain advantageously the cis(+)-2-(4-methoxyphenyl)-3-acetoxy-5-[2-(dimethylamino)ethyl]-2,3-dihydro-1,5-benzothiazepin-4(5H)-one by means of known methods.

The following example illustrates the invention without limiting the scope thereof.

EXAMPLE 4.7 Grams of 50% aqueous solution of L-lysine are added to a boiling suspension of 5.2 g of dl-α-2-hydroxy-3-(4-methoxyphenyl)-3-(2-aminophenylthio)propionic acid in 150 ml of methanol.

After drying under vacuum, 3 g of the L-lysine salt of the d-α-2-hydroxy-3-(4-methoxyphenyl)-3-(2-aminophenylthio)propionic acid with m.p.=137°–139° C. $[\alpha_D]^{22}+250°$ (C=0.5 in H$_2$O) are obtained.

This compound is dissolved in water and diluted acetic acid is added thereto until pH 4.5. The solid is collected by filtration and dried under vacuum. 1.85 g of d-α-2-hydroxy-3-(4-methoxyphenyl)-3-(2-aminophenylthio)propionic acid, m.p.=134°–135° C. $[\alpha_D]^{23}+340°$ (C=0.560 in CH$_3$OH) are obtained.

The mother liquors obtained by filtration of the L-lysine salt of the d-aminoacid are concentrated to small volume and the precipitated solid is filtered and dried.

There is obtained the L-lysine salt of the L-α-2-hydroxy-3-(4-methoxyphenyl)-3-(2-aminophenylthio)propionic acid which, after acidification with diluted acetic acid gives 1-α-2-hydroxy-3-(4-methoxyphenyl)-3-(2-aminophenylthio)propionic acid with an optical purity of about 90%.

We claim:

1. A process for the preparation of the d- or l-isomer of the α-2-hydroxy-3-(4-methoxyphenyl)-3-(2-aminophenylthio)propionic acid having formula I, through optical resolution of the dl racemic compound, characterized in that the dl-α racemic compound is satisfied with L-lysine, the two optically active salts are separated by fractional crystallization and the corresponding optically active acids are obtained by treatment with diluted organic or inorganic acids.

2. A process according to claim 1, characterized in that the reaction is carried out in alcoholic solvents.

3. A process according to claim 2 characterized in that the reaction is carried out in methanol or ethanol.

4. A process according to claim 1, characterized in that the L-lysine salt with the d-isomer of the α-2-hydroxy-3-(4-methoxyphenyl)-3-(2-aminophenylthio)propionic acid is isolated by filtration and that the L-lysine salt of the l-isomer of the α-2-hydroxy-3-(4-methoxyphenyl)-3-(2-aminophenylthio)propionic acid is recovered from the filtration mother liquors.

* * * * *